United States Patent [19]
Friedman

[11] 3,965,416
[45] June 22, 1976

[54] DIELECTRIC-CONSTANT MEASURING APPARATUS

[75] Inventor: Jay Friedman, Hermosa Beach, Calif.

[73] Assignee: Tylan Corporation, Torrance, Calif.

[22] Filed: May 28, 1974

[21] Appl. No.: 473,521

[52] U.S. Cl............................................. 324/58.5 B
[51] Int. Cl.²........................................ G01R 27/04
[58] Field of Search ........... 324/58.5 B, 58 B, 57 H, 324/57 PS, 57 R, 58 R, 58.5 R, 58.5 A

[56] References Cited
UNITED STATES PATENTS

| | | | |
|---|---|---|---|
| 3,162,807 | 12/1964 | Alford................................ | 324/58 B |
| 3,460,031 | 8/1969 | Evans et al. .................... | 324/58.5 A |
| 3,789,296 | 1/1974 | Caruso, Jr. et al............. | 324/58.5 B |
| 3,853,005 | 12/1974 | Schendel..................... | 324/58.5 B X |

Primary Examiner—Stanley T. Krawczewicz
Attorney, Agent, or Firm—Nilsson, Robbins, Dalgarn & Berliner

[57] ABSTRACT

Accurate and stable measurement of the dielectric constant of a substance or a mixture of substances is achieved by the use of an oscillatory system incorporating a shorted transmission line as a delay means, to cycle the system. The substance for which the dielectric constant is to be determined is introduced between or about the elements of the transmission line so as to vary the propagation rate or delay of signals through the transmission line. Accordingly, the frequency of oscillation for the system is indicative of the dielectric constant of the substance. Several specific forms of transmission lines, embodied as sensors are disclosed along with different forms of oscillator drivers.

13 Claims, 8 Drawing Figures

DIELECTRIC-CONSTANT MEASURING APPARATUS

BACKGROUND OF THE INVENTION

1. Field of the Invention

This invention relates to apparatus for measuring the dielectric constant of materials and more specifically to such instruments which utilize the application of R-F or microwave energy to a transmission line, in or around which a substance under investigation is introduced to vary the propagation characteristics of the transmission line.

2. Description of the Prior Art

Sensing the dielectric constant of a substance or material provides useful information in a variety of applications. In addition to indicating that specific characteristic of a substance, the information can be indicative of moisture content or other transitory conditions. For example, a measurement of the dielectric constant of a material-in-process may indicate moisture content as data for process control. A variety of such applications exist.

In the past the dielectric constants of various substances, fluid or solid, have been measured by such techniques as introducing the substance between the plates of a capacitor and noting the resulting change in capacitance. In using such a technique, if the substance under test has electrical conductivity, resulting electrical currents may cause serious errors in the dielectric-constant measurement. To offset that problem it has been customary to use high-frequency signals across the capacitor. With high-frequency excitation, the capacitor becomes physically small, however, with the attendant result that only small areas may be observed in a single measurement and the sensitivity of the system tends to be poor.

It has also been suggested that shorted transmission lines, driven at high frequencies, may be used for measuring dielectric constants. In such systems the shorted line is immersed in the substance which is being tested. If the transmission line is coaxial in nature a slot is provided in the line to probe along the transmission line for the null point. By detecting the null location, the dielectric constant of the substance may be calculated. Unfortunately, the null which has been mentioned is very broad. Consequently, accurate measurement of the dielectric constant is rather difficult, except under controlled laboratory conditions.

Another approach for determining the constant has been to measure the impedance change in the transmission line which occurs as the dielectric is introduced. This approach eliminates the insensitive-null problem (described above) but the relative separation of the transmission line conductors and potential coupling of the transmission line to other conductors in the vicinity of the transmission line are likely to cause first-order errors in the measurement.

Still another approach, again utilizing transmission lines for the measurement of dielectric constants, has been to introduce a fast rise-time pulse into a transmission line with the dielectric substance under investigation being in the space between the conductors of the transmission line. The initial pulse and the return pulses (reflected from discontinuities) are then presented on an oscilloscope. By mathematical computation, the speed of propagation of the known-frequency signal, first in air and then in the dielectric material being tested, is determined. This system though used effectively in laboratories is not readily adaptable to direct and convenient readout of the dielectric constant for a substance or material under investigation.

SUMMARY OF THE INVENTION

It is a general object of this invention to overcome the disadvantages indicated for the dielectric-constant measuring apparatus of the prior art.

It is an additional object of this invention to provide a dielectric-constant measuring instrument which will permit a direct readout of the dielectric constant for a substance.

It is a still further object of this invention to provide dielectric-constant measuring apparatus which is stable in its operation and easy to use for measurement of the dielectric characteristics of either fluid or solid substances.

The present invention contemplates a pulse delay oscillator, the frequency-determining element of which is a shorted transmission line into which the dielectric substance under investigation may be introduced conveniently. A driver pulses the line and is subsequently triggered by a reflection. The result is an oscillation, the frequency of which is representative of the dielectric constant of the substance.

BRIEF DESCRIPTION OF THE DRAWINGS

The features of the present invention which are believed to be novel are set forth with particularity in the appended claims. The present invention, both as to its organization and manner of operation, together with further objects and advantages thereof, may thus be understood with reference to the following description taken in conjunction with the accompanying drawings, in which:

DESCRIPTION OF THE PREFERRED EMBODIMENTS

Figure 1:
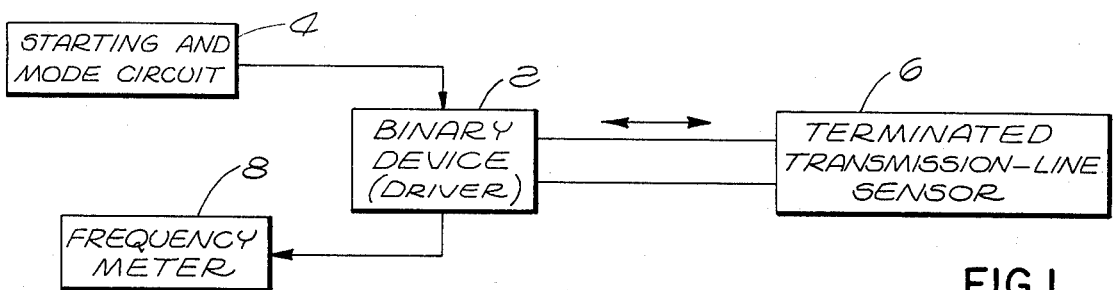
FIG. 1 is a block diagram of an instrument constructed in accordance with the present invention.

Referring initially to FIG. 1, the system is illustrated in a somewhat basic form. A driver or binary device 2 is actuated, as by a starting and mode circuit 4, to change in state and provide a synchronous positive feedback pulse to a binary device, driving a sensor 6. The dielectric substance under investigation (not shown) is contiguous to a transmission line (not shown) in the sensor 6, the line being terminated in a short to provide inverted reflections, as well known in the art. As the propagation rates of the initial pulse and the reflection are related to the dielectric characteristic of the substance under investigation (contiguous to the line) the time interval separating the pulse and the reflection is indicative of the dielectric constant of the substance under investigation.

Upon receiving the reflection (pulse) from the sensor 6, the binary device 2 is triggered to another change of state which introduces another pulse to the sensor 6. The cycle is repeated with the consequence that the binary device oscillates at a periodicity (and frequency) which is related to the dielectric constant of concern. A frequency meter 8 manifests the frequency of oscillation by the device 2 as a relative indication of dielectric constant.

Figure 2:
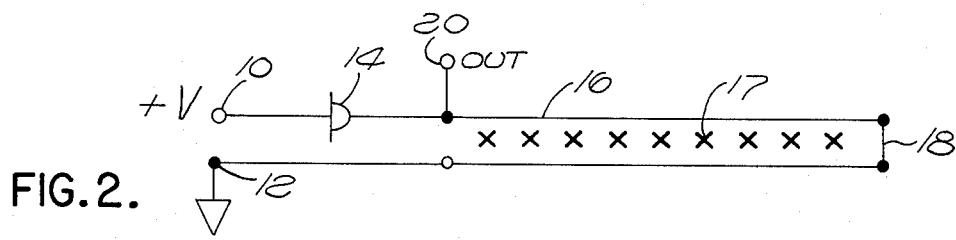
FIG. 2 is a schematic diagram of a simplified version of a measuring apparatus in accordance with the present invention.

The system may be variously implemented depending upon the selection of components and the economic considerations. A simple form is illustrated in FIG. 2 using a tunnel diode as a binary device. The theory of operation of a tunnel or Esaki diode is now well known but a brief description of it may be useful in analyzing the operation of the circuit of FIG. 2. The tunnel diode is a very fast switching device which relies upon the quantum mechanical tunneling of electrons across an energy level barrier. As an increasing positive voltage is applied to the anode of a tunnel diode, the current initially flows through the diode in a magnitude proportional to voltage. Initially, therefore, the tunnel diode appears as a resistor with a low magnitude of resistance. As the applied voltage increases, however, the diode current slope begins to decrease and, finally, current begins to decrease as applied voltage is increased.

In the operation of the system of FIG. 2, upon application of an appropriate voltage across a pair of terminals 10 and 12, a tunnel diode 14 produces a pulse which is propagated down a transmission line 16 encompassing a substance 17 of which the dielectric constant is of concern. Upon encountering a shorting element 18, the source pulse is reflected as a return pulse of inverted polarity. Upon reaching the tunnel diode 14, the return pulse or reflection changes the mode of operation of the tunnel diode 14 causing an additional pulse to be propagated down the transmission line 16. Oscillation is thus established at a frequency determined by the time of propagation of the initial and return pulses through the shorted transmission line 16. Consequently, the output frequency may be sensed at terminal 20 to indicate the dielectric constant of the substance 17. This circuit, while extremely simple, does suffer from some asymmetrical sensitivity and spurious oscillations resulting from noise.

Figure 3:
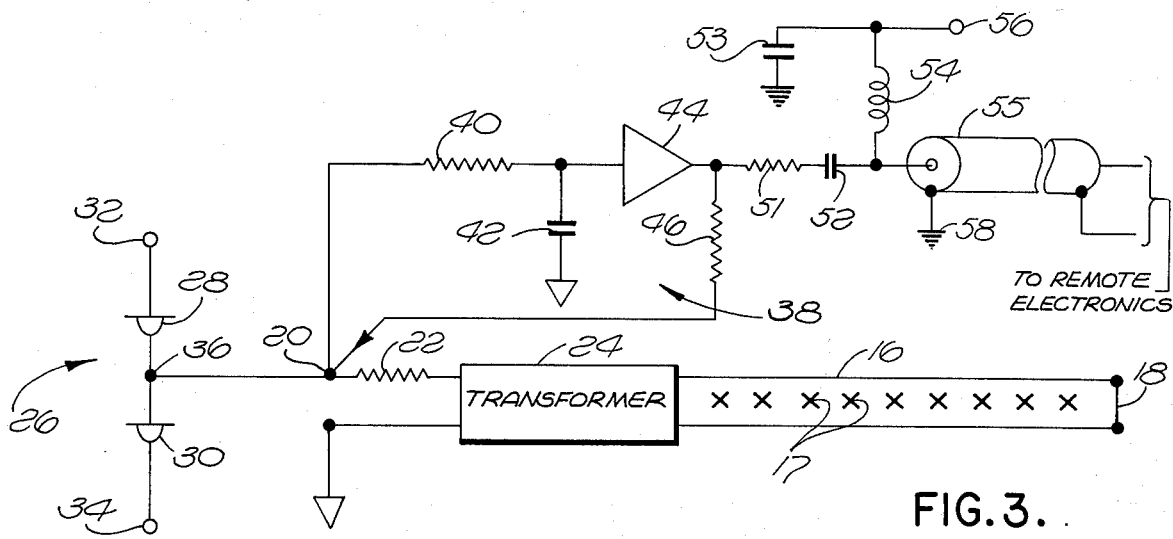
FIG. 3 is a schematic diagram showing another embodiment of a measuring apparatus according to the present invention, including several refinements representing a practical circuit.

In relation to the problem of noise, operation may be improved by a "boot-strap" technique that involves anticipating the delay time in a broad range, to condition the driver or binary device for a change of state. The technique involves delaying oscillations to provide signals that are early with reference to a following oscillation so as to qualify the time when such a following oscillation may occur. In the system of FIG. 3, the line 16 is similar to the previous description, however, is coupled through a resistor 22 and balun transformer 24 (optional) for supplying energy to and from the shorted transmission line 16. The balun transformer improves energy transfer to the sensor and provides sensor configuration freedom discussed later in this application. The detection and generation functions are performed by a driver 26 embodying tunnel or Esaki diodes 28 and 30. The diodes are serially connected between terminals 32 and 34 which are connected to an appropriate power supply. The junction point 36 between the diodes 28 and 30 is connected to the resistor 22 and to a qualifying delay circuit 38 which returns an inverted pulse to the junction point 36.

Considering the operation of the system of FIG. 3, if the voltage applied to the tunnel diode 28 is such that it is operating in the negative conductance region while at the same time the voltage applied to the tunnel diode 30 (through the terminal 36) is such that the tunnel diode 30 is operating in the low voltage resistor-like region, then upon a sufficient voltage change at the junction point 36, a pulse will be generated as the tunnel diodes reverse states and that pulse will be propagated down transmission line 16.

The diodes 28 and 30, accordingly, function as driver or a bistable device 26 to sense pulse reflections above a predetermined level and thereupon to change state and provide another pulse. To reduce the effects of noise, the bistable device 26 is designed to be relatively insensitive so that it requires energy in addition to the reflected pulse received through the resistor 22. The additional energy is provided from the delay circuit 38 (coinciding to circuit 4, FIG. 1) after an appropriate initial time delay. Specifically, the bistable device 26 changes state upon receiving a reflected pulse through the resistor 22, providing it is supported by a delayed and inverted pulse from the delay circuit 38.

In actual practice, it has been found that the RC time constant of the combination of the resistor 40 and a condenser 42 in the delay circuit 38 should produce a lag of about 60° to 120°. The inverting amplifier 44 reverses the polarity of this phase-delayed signal to produce a phase lead of 120° to 60° in the energy fed back to the bistable device 26. This feedback (at a 120° to 60° phase lead) conditions the sustained oscillation at a fundamental frequency determined by the effective length of the shorted transmission line 16. The advantage of this circuit is its insensitivity to extraneous noise, by supporting oscillation of the correct mode. Accordingly, the frequency of oscillation of the circuit (which may be sensed at the output of 44) is more accurately reflective of the dielectric constant of the substance 17.

It is possible from FIG. 3 to appreciate an important feature of the present invention, specifically, that the pulse delay oscillator is proximate to the sensor, which is important for accuracy of measurement. Also, the signal indicating the frequency of oscillation is provided to remote readout electronics by way of the transmission line 55. Resistor 51 and capacitor 52 couple signal to the output line 55 while an R-F choke 54 and a bypass capacitor 53 isolate a power supply voltage 56 relative to a power ground 58. The power for operating the oscillating system is carried by the transmission line, thus, a single two-conductor transmission line (open line or coaxial) may be used for power input and oscillator-signal output from the system.

Figure 4:
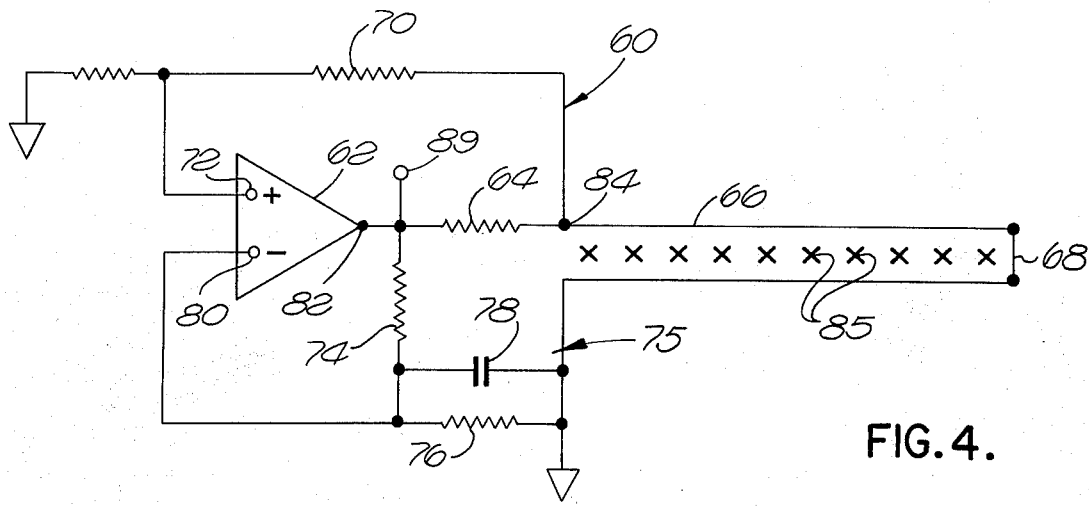
FIG. 4 is a diagram, in schematic form, showing a general configuration of a pulse delay oscillator which may be used in dielectric measuring apparatus according to the present invention.

A system that is somewhat related to that of FIG. 3 is depicted in FIG. 4 as another alternative. Specifically, viewed as an oscillator, the system includes a saturating amplifier 62 which is coupled through a terminating resistance 64 to a transmission line 66. A resistor 70 provides positive feedback from the output of amplifier 62 to its input terminal 72. A network 75 made up of resistors 74 and 76 in combination with a condenser 78 provides negative feedback from the output of the amplifier 62 to its input terminal 80.

When power is applied across the terminals 72 and 80, the amplifier 62 produces a pulse at its output which is a result partially of an initial offset and partially because of the positive feedback through the resistor 70. The pulse which is generated at the output terminal 82 of the amplifier 62 is coupled through the terminating resistor 64 to a shorted transmission line 66. The pulse generated by the amplifier 62 begins to propagate down the transmission line 16 and at the same time negative feedback from the output terminal 82 to input terminal 80 begins to occur. The resistors 74 and 76 may be chosen so that, after a small delay (caused by the time required for the charging of the condenser 78) the output signal from the amplifier 62 will reverse in polarity when the voltage applied through the resistor 70 from input terminal 84 of transmission line 16 reaches one half of its original magnitude, or other suitable level.

As the initial pulse generated by the amplifier 62 reaches the shorting element 68, a pulse of opposite polarity begins to propagate from the shorting element back towards the amplifier 62. In the middle of the rise time of the return pulse, the amplifier 62 senses the returned pulse and supports the change in voltage which has occurred, as a result of which a new pulse is propagated down the transmission line 66. That pulse being of opposite polarity to the initial pulse propagated down the line 66.

This process continues and a square wave signal is generated, the frequency of which may be observed from the amplifier 62 and which is dependent upon the propagation time for a pulse moving through transmission line 66. Of course, the propagation time of a pulse through transmission line 66 depends upon the nature of the dielectric substance 85 introduced in the transmission line. Consequently, by observing the frequency of the oscillating system, as at terminal 89, the dielectric constant of the substance 85 may be measured.

Figure 5:
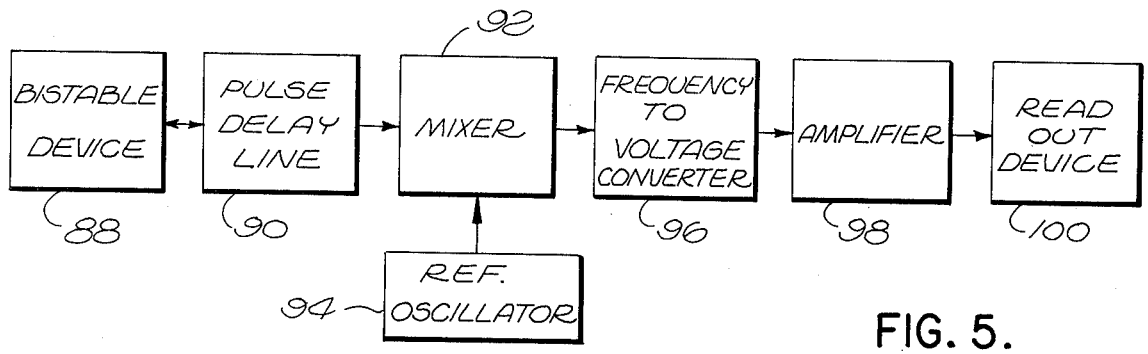
FIG. 5 is a block diagram of a completed form of the measuring apparatus hereof.

Turning now to an embodiment of the present invention implemented as a complete system, reference will be had to FIG. 5. In that regard, it may be desirable to detect minor changes in dielectric constants, as for example when the moisture content of a dielectric material is to be determined. A driver or bistable device 88 and a pulse-delay line 90 operate in the manner described above; however, the output signal from the line 90 is heterodyned in a mixer 92 against the signal from a reference oscillator 94. The difference signal is fed to a frequency-to-voltage converter 96 operating at a lower frequency for more convenient sensing. Further, greater effective gain of the system is realized. Even greater accuracy in measurement of the dielectric constant may be obtained if a "divide by N" counter is interposed between the output of the mixer 92 and the input of converter 96. As illustrated, the output of converter 96 is fed through an amplifier 98 to an analog or digital (whichever is appropriate) readout device 100 for direct dielectric constant indication.

Figure 6:
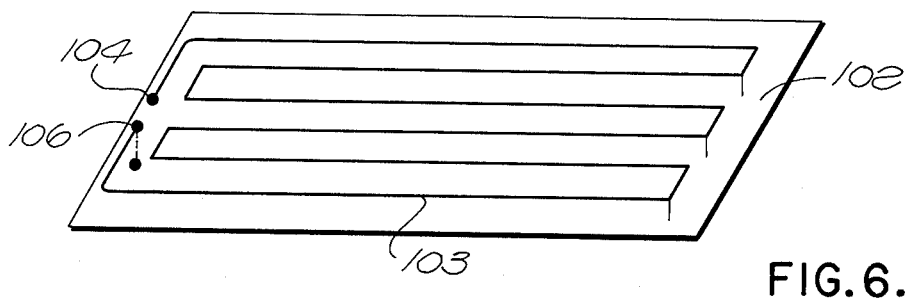
FIG. 6 is a perspective view of an illustrative sensor component of the dielectric measuring apparatus according to the present invention.

It may be seen from the above, that the present system may be variously embodied to accommodate different objectives. The driver portion of the oscillatory system may comprise various amplifiers, diode devices or a flip-flop structure. Similarly, the transmission line also may take a variety of different forms depending on specific applications. For example, as suggested above, the line may comprise simply a pair of supported conductors terminated by a shorting element at one end. The space between the conductors may then receive the substance of interest for measurement of its dielectric constant. Other structural forms of the line may involve a ground plane and folded lines. Specifically, in FIG. 6, a transmission line is made up of a folded conductor 103 supported above a ground plane 102. Both of the terminals 104 and 106 may be kept above ground (with a central termination) or one of the terminals, such as terminal 106 may be converted to the ground plane 102 as indicated.

Figures 7, 8:
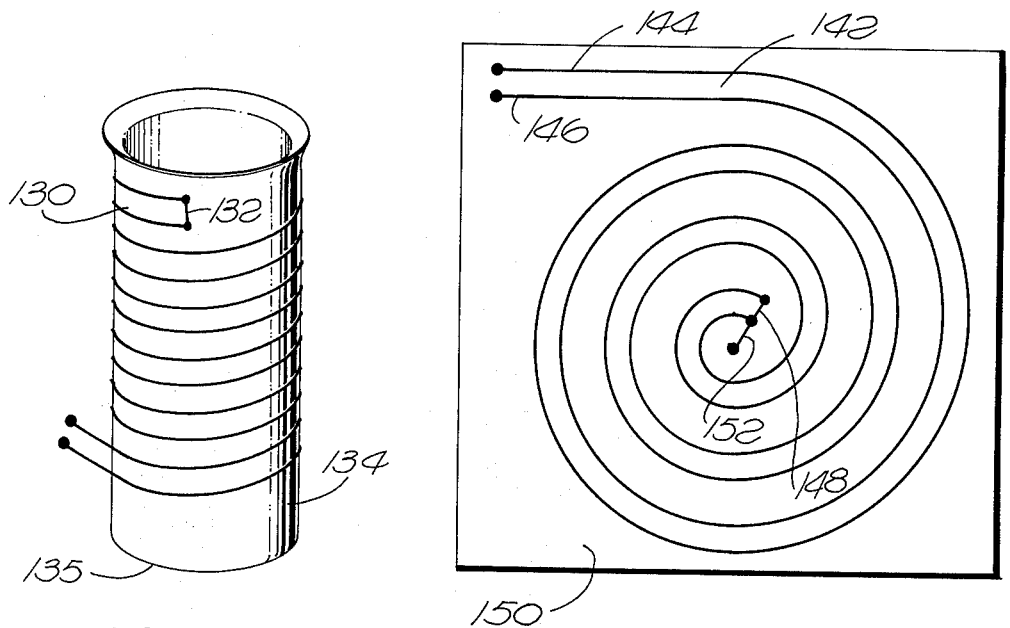
FIG. 7 is a perspective view of another illustrative sensor component configuration which is cylindrical in nature and which may be utilized in connection with apparatus of the present invention.
FIG. 8 is a perspective view of an additional configuration for a sensor component, spiral in nature, to be used in connection with apparatus of the present invention.

In FIG. 7, a two-element transmission line 130 having shorting element 132 is wound about an insulating cylinder 134 which may be hollow and have bottom 135 to form a cup, or which may be open and act as a pipe. Liquid or granular solids, the dielectric constants of which are to be measured, may be placed within the cylinder 134, or passed through. A conductive cylinder, not shown, may be placed around or within the combination of cylinder 134 and transmission line 130. In this configuration, one element of transmission line 130, as well as shorting element 132, may be connected or grounded to the conductive cylinder.

In FIG. 8, a two-conductor transmission line 142 comprises transmission line conductors 144 and 146 and shorting element 148. Transmission line 142 may be supported above a ground plane 150, to which shorting element 148 may be grounded as by conductor 152. Further, either transmission line element 144 or transmission line element 146 may also be grounded to plane 150. Of course, the configuration does not have to be spiral; it may be folded. Also, a spiral version of the folded transmission line sensor of FIG. 6 may also be useful, as would a two element folded version of FIG. 6.

Two element transmission line sensors provide certain advantages in conjunction with a balun transformer (transformer 24 of FIG. 3). In the case of a folded or spiral two element line supported over a plane, a laminar of dielectric may be placed between the plane and sensor. The balun transformer optimizes energy transfer from a single ended system (electronics) to a balanced system (transmission line). The plane tends to keep the field uniform between the transmission line and the plane, allowing relative movement of the dielectric between plane and line to cause little change in instrument reading. Also, since the system is balanced the ground plane need not be grounded electrically: a connection which would be difficult to make in the case of textile tentnor frame applications where frame elements would make a high quality ground connection possible only through a hole in the laminar material under measurement.

A two element line may also be used without the addition of a ground plane. If a balun transformer is used here then unwanted signals will not couple from the sensor to electronics signal ground, and again, energy transfer may be optimized.

In general, the dielectric under measurement, if spacing is well defined as in a liquid measurement using the sensor of FIG. 7, the dielectric may be outside of (or inside of) both the transmission line and the plane, but in juxtaposition to the transmission line, or the line may be immersed.

While there have been described hereinbefore specific embodiments of dielectric constant measuring apparatus, it will be appreciated that the invention is not limited thereto. Accordingly, any and all modifications, variations or equivalent arrangements which may occur to those skilled in the art should be considered to be within the scope of the invention as defined in the invention claims.

What is claimed is:

1. Apparatus for the measurement of the dielectric constant of a substance, comprising:
   a driver device, including a tunnel diode operating to change the state of said device, said device actuable by applied pulses to reverse states and thereby provide drive pulses;
   a sensor for placement contiguous to said substance, said sensor being connected to receive drive pulses from said driver device and including a transmission line terminated to provide reflections of received pulses related in time to the dielectric constant of said substance, said reflections being applied as pulses to said driver device; and
   means for manifesting the time relationship between said pulses and reflections to indicate said dielectric constant.

2. An apparatus according to claim 1 wherein said driver device and said sensor are interconnected such that said reflections trigger said driver device to establish oscillation at a frequency representative of said dielectric constant.

3. Apparatus according to claim 1 further including a phase shift circuit for conditioning said driver device to be triggered during select intervals.

4. Apparatus according to claim 3 wherein said phase shift circuit includes a voltage-inverting amplifier and a delay circuit.

5. An apparatus according to claim 1 wherein said driver device and said sensor are interconnected such that said reflections trigger said driver device to establish oscillation at a frequency representative of said dielectric constant and wherein said means for manifesting includes signal means for indicating the frequency of said oscillation.

6. An apparatus according to claim 4 wherein said means for manifesting includes means for heterodyning signals at said frequency of said oscillation to signals of a different frequency for measurement.

7. An apparatus according to claim 4 wherein said means for manifesting includes a frequency-to-voltage converter connected to said signal means.

8. Apparatus according to claim 1 wherein said transmission line includes a sheet of conductive material defining a ground plane and at least one conductor mounted in spaced apart relationship to said sheet.

9. Apparatus according to claim 1 wherein said transmission line comprises a container and conductor means affixed thereon.

10. An apparatus according to claim 1 wherein said transmission line includes two sheets of parallel conductive material, enclosing said transmission line.

11. An apparatus according to claim 1 further including a transformer coupling said driver device to said sensor.

12. An apparatus for measuring physical characteristics of a substance under observation by electrical reflections comprising:
    a sensor for placement contiguous to said substance under observation, said sensor including a transmission line to provide reflections of received pulses which reflections are time displaced from said received pulses to indicate a characteristic of said substance under observation;
    a change of state driver means including at least one tunnel diode to accomplish rapid switching and which relies on the quantum mechanical tunneling of electrons across an energy level barrier therein, said change of state driver means being connected to said sensor for providing said received pulses to said transmission line upon a change of state and to change state upon receiving said reflections from said transmission line; and
    means for manifesting the frequency of changes of state by said driver means as a characteristic of said substance.

13. An apparatus according to claim 12 wherein said transmission line includes termination means to provide reflections of received pulses.

* * * * *